(12) United States Patent
Koitabashi et al.

(10) Patent No.: US 9,986,900 B2
(45) Date of Patent: Jun. 5, 2018

(54) ENDOSCOPE

(71) Applicant: OLYMPUS CORPORATION, Tokyo (JP)

(72) Inventors: Masanobu Koitabashi, Hachioji (JP); Kazuhiko Hino, Hachioji (JP); Shiho Kabasawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 14/195,211

(22) Filed: Mar. 3, 2014

(65) Prior Publication Data

US 2014/0200513 A1 Jul. 17, 2014

Related U.S. Application Data

(63) Continuation of application No. PCT/JP2013/076857, filed on Oct. 2, 2013.

(30) Foreign Application Priority Data

Oct. 22, 2012 (JP) .................................. 2012-233023

(51) Int. Cl.
*A61B 1/04* (2006.01)
*A61B 1/005* (2006.01)
*A61B 1/00* (2006.01)

(52) U.S. Cl.
CPC .......... *A61B 1/0055* (2013.01); *A61B 1/0016* (2013.01); *A61B 1/0052* (2013.01); *A61B 1/0057* (2013.01); *A61B 1/00066* (2013.01)

(58) Field of Classification Search
CPC . A61B 1/00066; A61B 1/0052; A61B 1/0057; A61B 1/0055; A61B 1/0016

(Continued)

(56) References Cited

U.S. PATENT DOCUMENTS 1,958,656 A * 5/1934 Buerger ................. A61B 1/307
600/106
4,344,092 A * 8/1982 Miller ........................... 348/331

(Continued)

FOREIGN PATENT DOCUMENTS

JP 64-46001 A 3/1989
JP 8-299256 A 11/1996

(Continued)

OTHER PUBLICATIONS

Extended Supplementary European Search Report dated Jun. 15, 2016 in European Application No. 13 84 8795.4.

*Primary Examiner* — Anhtuan T. Nguyen
*Assistant Examiner* — Jae Woo
(74) *Attorney, Agent, or Firm* — Scully, Scott, Murphy & Presser, P.C.

(57) ABSTRACT

A first housing region A which is provided in the operation portion and in which a bending drive mechanism is housed, a second housing region B which is provided in the operation section and in which a flexible member is housed, and a third housing region C which is provided in the operation portion and in which an electric part is housed are provided, the first housing region A and the second housing region B are located to be lined up in an orthogonal direction Q, and the third housing region C is located to be adjacent to both of the first housing region A and the second housing region B so that a first boundary line T1 is orthogonal to a second boundary line T2.

13 Claims, 10 Drawing Sheets

(58) Field of Classification Search
USPC .................................. 600/128, 130, 131
See application file for complete search history.

(56) References Cited

U.S. PATENT DOCUMENTS

| | | | |
|---|---|---|---|
| 4,349,032 A * | 9/1982 | Koyata | 600/139 |
| RE31,290 E * | 6/1983 | Moore et al. | 600/109 |
| 4,552,129 A * | 11/1985 | Utsugi et al. | 600/131 |
| 4,741,327 A * | 5/1988 | Yabe | A61B 1/00177 348/65 |
| 5,131,382 A * | 7/1992 | Meyer | A61B 1/042 600/104 |
| RE34,110 E * | 10/1992 | Opie | A61B 1/00071 600/123 |
| 5,411,020 A * | 5/1995 | Ito | 600/146 |
| 5,587,736 A * | 12/1996 | Walls | 348/65 |
| 5,609,561 A * | 3/1997 | Uehara et al. | 600/112 |
| 5,993,380 A * | 11/1999 | Yabe et al. | 600/121 |
| 6,328,730 B1 * | 12/2001 | Harkrider, Jr. | 604/523 |
| 6,503,196 B1 * | 1/2003 | Kehr et al. | 600/176 |
| 6,641,530 B2 * | 11/2003 | Mitsumori | 600/167 |
| 7,108,656 B2 * | 9/2006 | Fujikawa et al. | 600/102 |
| 8,282,543 B2 * | 10/2012 | Ishiguro et al. | 600/104 |
| 8,313,427 B2 * | 11/2012 | Ishii | 600/170 |
| 8,353,821 B2 * | 1/2013 | Segawa | A61B 1/0011 600/128 |
| 8,459,844 B2 * | 6/2013 | Lia | A61B 1/0661 362/326 |
| 8,696,554 B2 * | 4/2014 | Omori | 600/178 |
| 8,961,401 B2 * | 2/2015 | Takeuchi et al. | 600/141 |
| 8,998,801 B2 * | 4/2015 | Okazaki | B25J 18/06 600/145 |
| 9,028,397 B2 * | 5/2015 | Naito | 600/150 |
| 9,050,052 B2 * | 6/2015 | Irie | |
| 2002/0115907 A1 * | 8/2002 | Mitsumori | 600/131 |
| 2005/0059859 A1 * | 3/2005 | Konstorum | 600/130 |
| 2005/0267335 A1 * | 12/2005 | Okada et al. | 600/173 |
| 2006/0264709 A1 * | 11/2006 | Fujimori et al. | 600/130 |
| 2009/0012358 A1 * | 1/2009 | Ichihashi | A61B 1/00105 600/110 |
| 2009/0105536 A1 * | 4/2009 | Honda et al. | 600/106 |
| 2009/0287043 A1 * | 11/2009 | Naito et al. | 600/104 |
| 2009/0292169 A1 | 11/2009 | Mitani et al. | |
| 2010/0022837 A1 * | 1/2010 | Ishiguro | A61B 17/29 600/127 |
| 2010/0160730 A1 * | 6/2010 | Konomura | 600/114 |

FOREIGN PATENT DOCUMENTS

| | | |
|---|---|---|
| JP | H09-164111 A1 | 6/1997 |
| JP | 9-173278 A | 7/1997 |
| JP | 11-332818 A | 12/1999 |
| JP | 2001-305435 A | 10/2001 |
| JP | 2003-190078 A | 7/2003 |
| JP | 2009-005836 A | 1/2009 |

* cited by examiner

ENDOSCOPE

CROSS REFERENCE TO RELATED APPLICATION

This application is a continuation application of PCT/JP2013/076857 filed on Oct. 2, 2013 and claims benefit of Japanese Application No. 2012-233023 filed in Japan on Oct. 22, 2012, the entire contents of which are incorporated herein by this reference.

BACKGROUND OF THE INVENTION

1. Field of the Invention

The present invention relates to an endoscope including an insertion portion to be inserted into a subject and an operation portion connected in series to a proximal end in an insertion direction of the insertion portion to be grasped and operated by an operator.

2. Description of the Related Art

In recent years, an endoscope has been widely used in a medical field and an industrial field. With an endoscope for use in the medical field, it is possible to observe an organ inside a body cavity as a subject by inserting an elongated insertion portion into the body cavity, and as necessary perform various kinds of treatment using a treatment instrument that is inserted into a treatment instrument insertion channel provided in the endoscope.

Further, with an endoscope for use in the industrial field, by inserting an elongated insertion portion of the endoscope into an object such as a jet engine or pipes in a factory, it is possible to perform an examination such as an observation of flaws or corrosion or the like at a site to be examined inside the object, and various kinds of treatment.

Further, an image pickup unit for picking up an image inside the subject or object is provided in a distal end portion which is located on a proximal end side in an insertion direction of the insertion portion of the endoscope (hereinafter referred to simply as "proximal end side"). An image of a site of the subject or object which is picked up by the image pickup unit is converted into an electric signal (hereinafter referred to as "image pickup signal") by the image pickup unit. Thereafter, the image pickup signal is transmitted through a signal cable having one end connected to the image pickup unit inside the insertion portion of the endoscope, an operation portion connected in series to a proximal end in the insertion direction of the insertion portion (hereinafter simply referred to as "proximal end"), a universal cord extended from the operation portion and a connector provided at an extended end of the universal cord, and further transmitted to an external apparatus by the connector being connected to the external apparatus and is displayed on a monitor provided at the external apparatus.

Furthermore, in the operation portion, a bending drive mechanism for bending a bending portion provided at a proximal end of the distal end portion on a distal end side of the insertion portion, a light guide for transmitting illumination light to a distal end in the insertion direction of the insertion portion (hereinafter simply referred to as "distal end"), and various types of tubes for supplying a liquid and an air to the distal end of the insertion portion.

Here, in Japanese Patent Laid-Open Publication No. 2009-005836, there is disclosed a configuration in which a motor used in electrically driving the bending drive mechanism and electric parts such as a substrate for controlling drive of the motor are provided in the operation portion.

Besides, as the electric part provided in the operation portion, an electric substrate is provided for preventing the image pickup signal from being attenuated while the image pickup signal transmits from the image pickup unit to the external apparatus because the signal cable is too long. In other words, in order to obtain an image of higher quality there are provided an electric substrate that is electrically connected to the signal cable at an intermediate position in the operation portion and amplifies the image pickup signal, and an electric substrate for driving and controlling a light source in a case where the light source is provided in the operation portion.

SUMMARY OF THE INVENTION

An endoscope according to an aspect of the present invention includes an insertion portion to be inserted into a subject and an operation portion provided in series at a proximal end of the insertion portion in an insertion direction to be grasped and operated by an operator, and the endoscope includes: a first housing region which is provided in the operation portion and in which a bending drive mechanism for bending a bending portion provided at the insertion portion is housed; a second housing region which is provided in the operation section and in which a flexible member is housed, the flexible member being solid or hollow and elongated along the insertion direction and being inserted through at least the insertion portion and the operation portion; and a third housing region which is provided in the operation portion and in which an electric part is housed, wherein the first housing region and the second housing region are located to be lined up in a direction orthogonal to the insertion direction, and the third housing region is located to be adjacent to both of the first housing region and the second housing region so that a first boundary line between the first housing region and the second housing region is orthogonal to a second boundary line between the first and second housing regions and the third housing region.

DETAILED DESCRIPTION OF THE PREFERRED EMBODIMENTS

Figure 1:
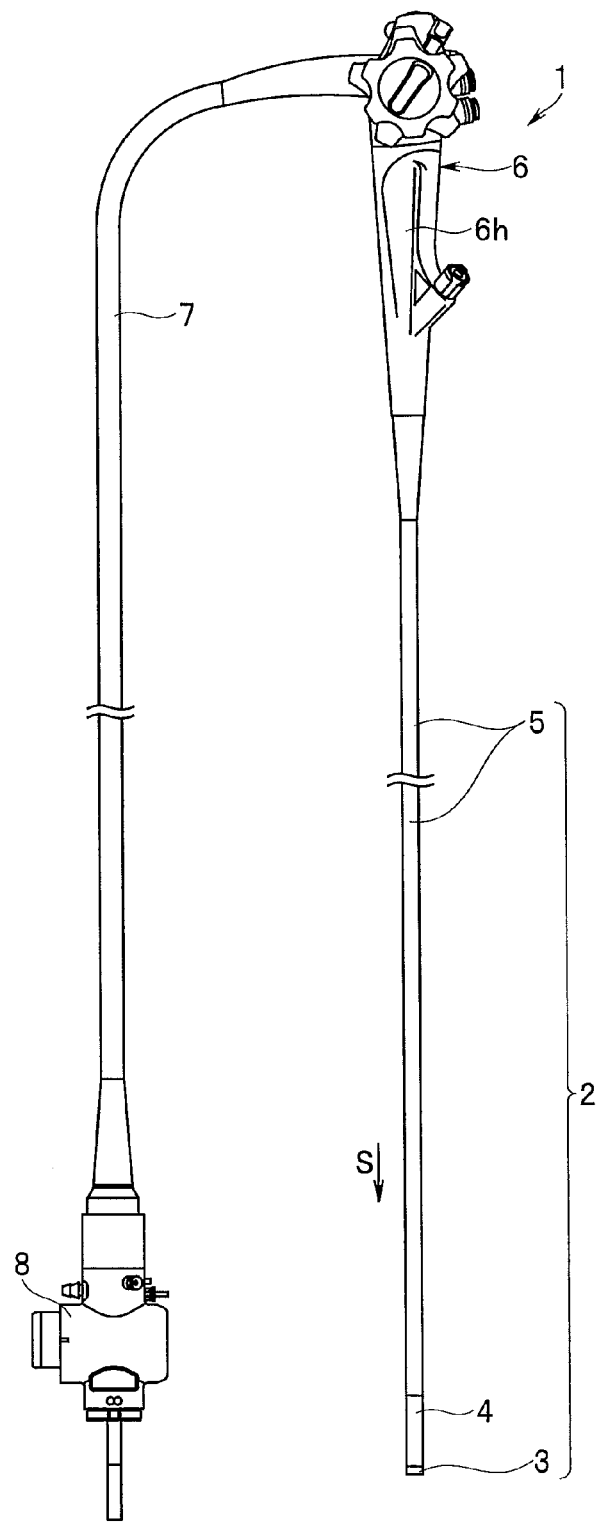
FIG. 1 is a view showing an endoscope according to a first embodiment of the present invention.

Hereinafter, embodiments of the present invention will be described referring to the drawings.

First Embodiment

Figure 2:
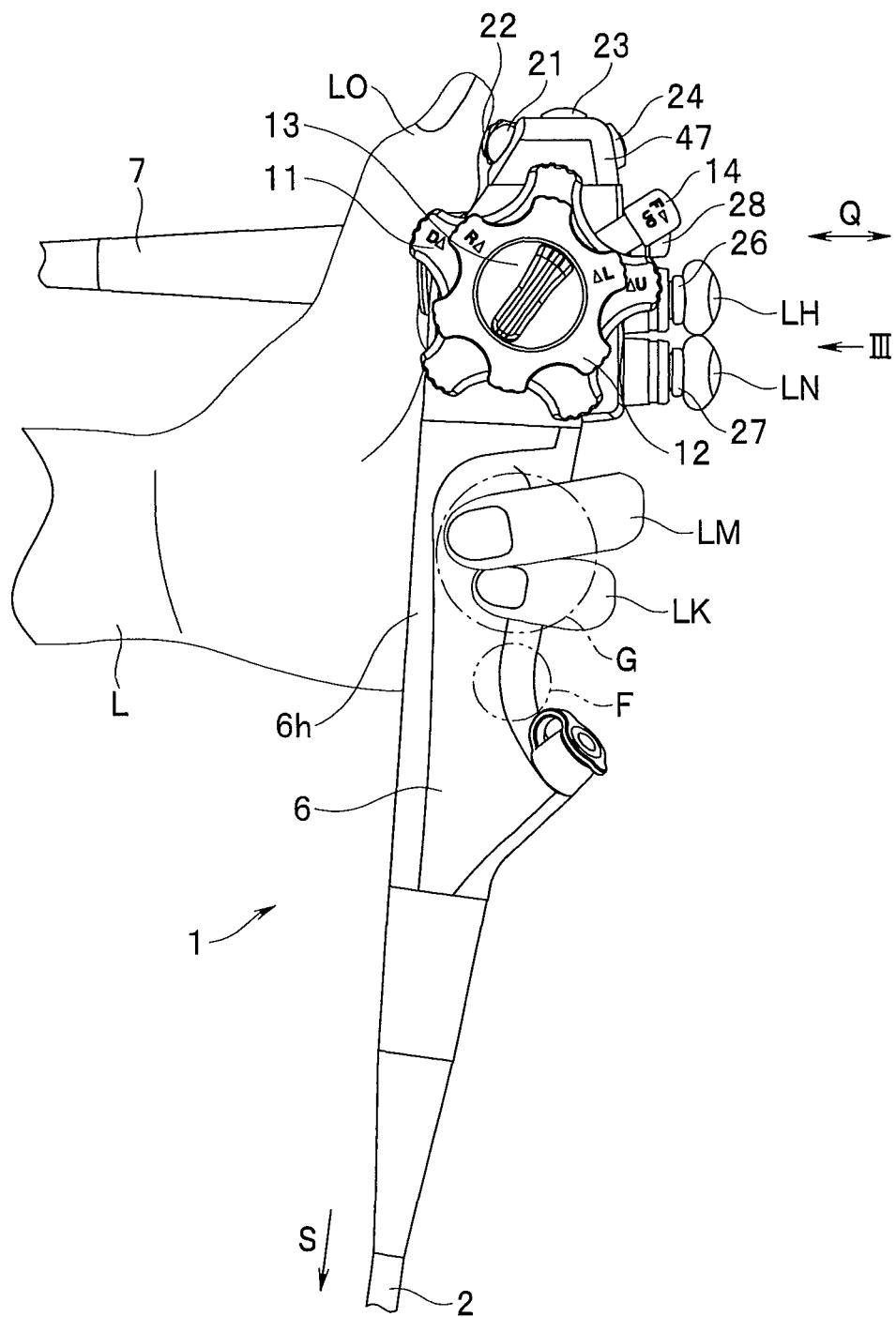
FIG. 2 is an enlarged view showing a state in which an operation portion of the endoscope in FIG. 1 is grasped by a left hand of an operator.
Figure 3:
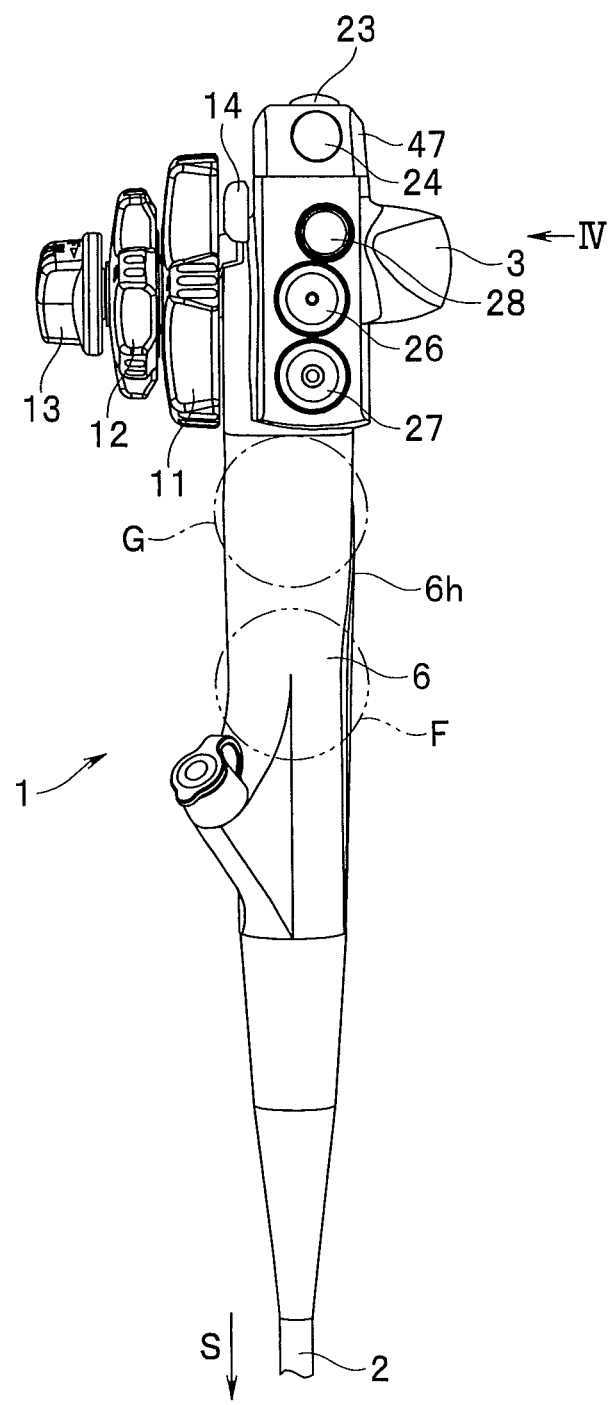
FIG. 3 is a view of the operation portion of the endoscope in FIG. 2 when viewed from direction III in FIG. 2.
Figure 4:
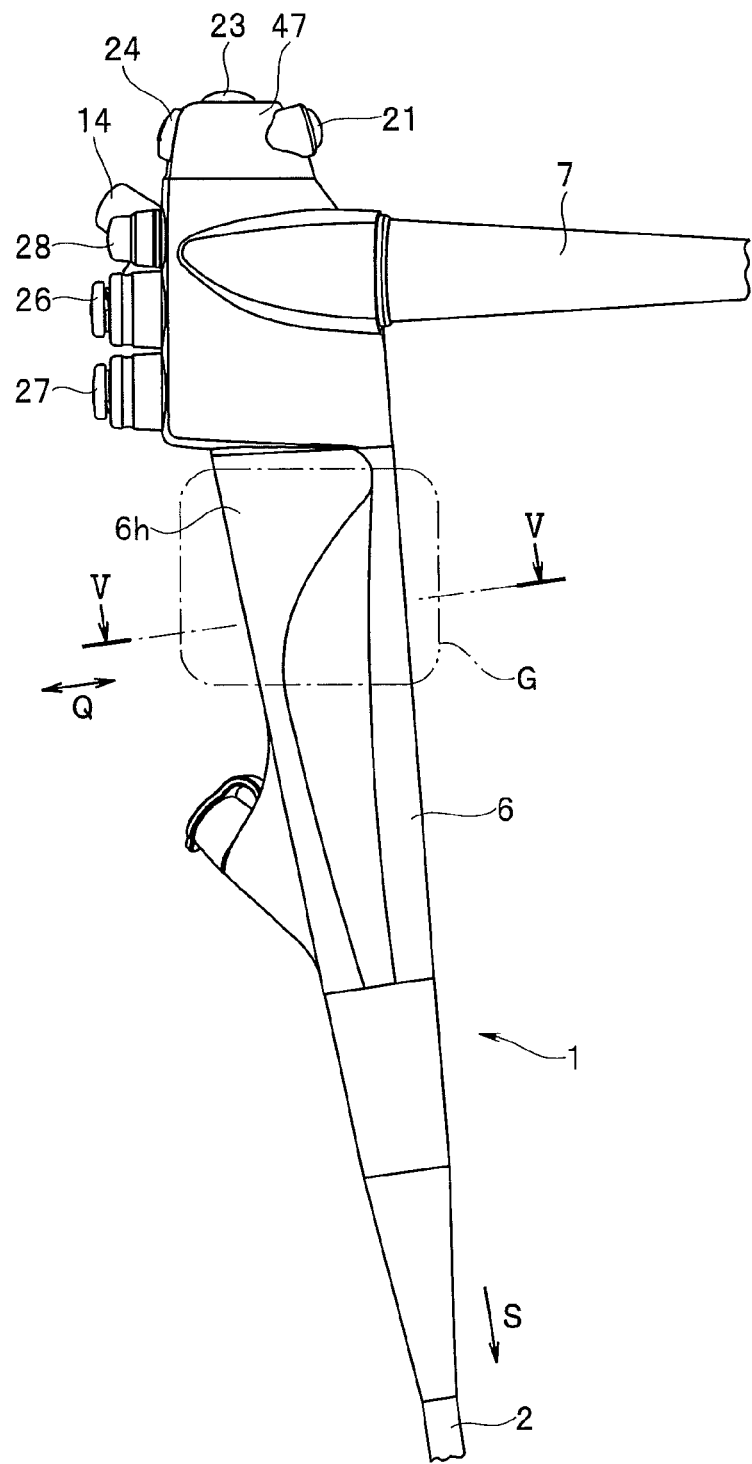
FIG. 4 is a view of the operation portion of the endoscope in FIG. 3 when viewed from direction IV in FIG. 3.

FIG. 1 is a view showing an endoscope according to a first embodiment of the present invention, FIG. 2 is an enlarged view showing a state in which an operation portion of the endoscope in FIG. 1 is grasped by a left hand of an operator, FIG. 3 is a view of the operation portion of the endoscope in FIG. 2 when viewed from direction III in FIG. 2, and FIG. 4 is a view of the operation portion of the endoscope in FIG. 3 when viewed from direction IV in FIG. 3.

As shown in FIG. 1, an endoscope 1 is configured to include, as principal parts, an insertion portion 2 to be inserted into a subject, an operation portion 6 which is provided in series at a proximal end of the insertion portion 2 and is grasped and operated by an operator, a universal cord 7 which is extended from the operation portion 6, and a connector 8 provided at an extended end of the universal cord 7.

Besides, the connector 8 is connectable to a light source apparatus and a video processor, etc. which are already known and not shown, and thereby the endoscope 1 is configured to be connectable to peripheral apparatuses.

The insertion portion 2 is configured to mainly include, from a distal end thereof, a distal end portion 3, a bending portion 4 and a flexible tube portion 5 in this order.

The bending portion 4 is operated to bend in four directions of up, down, right and left, for example, by bending operation knobs 11 and 12 (see FIG. 2) provided at the operation portion 6, and is provided between the distal end portion 3 and the flexible tube portion 5.

The operation portion 6 has a grasping portion 6h which is formed as a portion to be grasped by a palm, a middle finger LN, a ring finger LM, a little finger LK of a left hand L of the operator on an exterior member 6g (see FIG. 5) of the operation portion 6 on a side of the insertion portion 2 in an insertion direction S, as shown in FIG. 2, and further various operation switches, knobs, levers and lugs are provided at a region on a proximal end side with respect to the grasping portion 6h in the insertion direction S (hereinafter referred to simply as "proximal end side").

Specifically, as shown in FIGS. 2-4, a switch box 47 is provided at an end part of the operation portion 6 remote from the insertion portion 2 in the insertion direction S.

As shown in FIG. 2, a release switch button 21 for instructing recording of an image picked up by an image pickup unit which is provided, for example, in the distal end portion 3 and not shown, and a zoom switch button 22, for example, of the image pickup unit as mentioned above are provided on a surface of the switch box 47 on a side of the universal cord 7.

Besides, when an end part of the universal cord 7 is grasped by the left hand L of the operator as shown in FIG. 2, the switch buttons 21 and 22 are operated by a thumb LO of the left hand L.

Further, on a top surface of the switch box 47, as shown in FIGS. 2-4, a power switch button 23 for turning on/off a power supply of the endoscope 1, for example, is provided and further an iris switch button 24 for changing a light measurement method, for example, is provided on a surface opposite to the surface on which the switch buttons 21 and 22 are provided.

Besides, the switch buttons 23 and 24 are operated by an index finger LH of the left hand L when the operation portion 6 is grasped as shown in FIG. 2.

Further, as shown in FIGS. 2 and 3, the bending operation knobs 11 and 12 for bending the bending portion 4 are provided on a surface of the operation portion 6 adjacent to the surface on which the switch buttons 21 and 22 are provided, the surface on which the switch button 23 is provided and the surface on which the switch button 24 is provided, at a location which is proximal with respect to the grasping portion 6h and distal with respect to the switch box 47.

The bending operation knob 11 is a knob to be operated to rotate for bending the bending portion 4 in up and down directions and is configured such that a rotated position is fixed by an operation of a rotated position fixing lever 14.

Further, the bending operation knob 12 is a knob to be operated to rotate for bending the bending portion 4 in right and left directions and is configured such that a rotated position is fixed by an operation of a rotated position fixing lug 13.

The bending operation knobs 11 and 12 are operated by the thumb LO when the operation portion 6 is grasped as shown in FIG. 2.

Furthermore, as shown in FIGS. 2-4, a freeze switch button 28 for instructing a standstill of an image picked up by the image pickup unit, for example, a known air/water feeding operation switch button 26, and a known suction operation switch button 27 are provided on a surface of the operation portion 6 which is adjacent to the surface on which the bending operation knobs 11 and 12 are provided and which is distal with respect to the switch button 24, at a location which is proximal with respect to the grasping portion 6h and distal with respect to the switch box 47.

The freeze switch button 28, the air/water feeding operation switch button 26 and the suction operation switch button 27 are operated by the index finger LH and the middle finger LN when the operation portion 6 is grasped as shown in FIG. 2

Besides, hereinafter, as shown by the dashed line in FIG. 2 and FIG. 3, a region grasped by the ring finger LM and the little finger LK (and also the middle finger LN, not shown in FIG. 2, depending on the circumstances) of the left hand L in the grasping portion 6h of the operation portion 6 and, as shown by the dashed line in FIG. 4, a region in contact with the palm of the left hand L in the grasping portion 6h of the operation portion 6 are referred to as a covering region G by the fingers of the operator, and a region which is located distal with respect to the covering region G and not in contact with the fingers of the operator is referred to as a non-covering region F.

Figure 5:
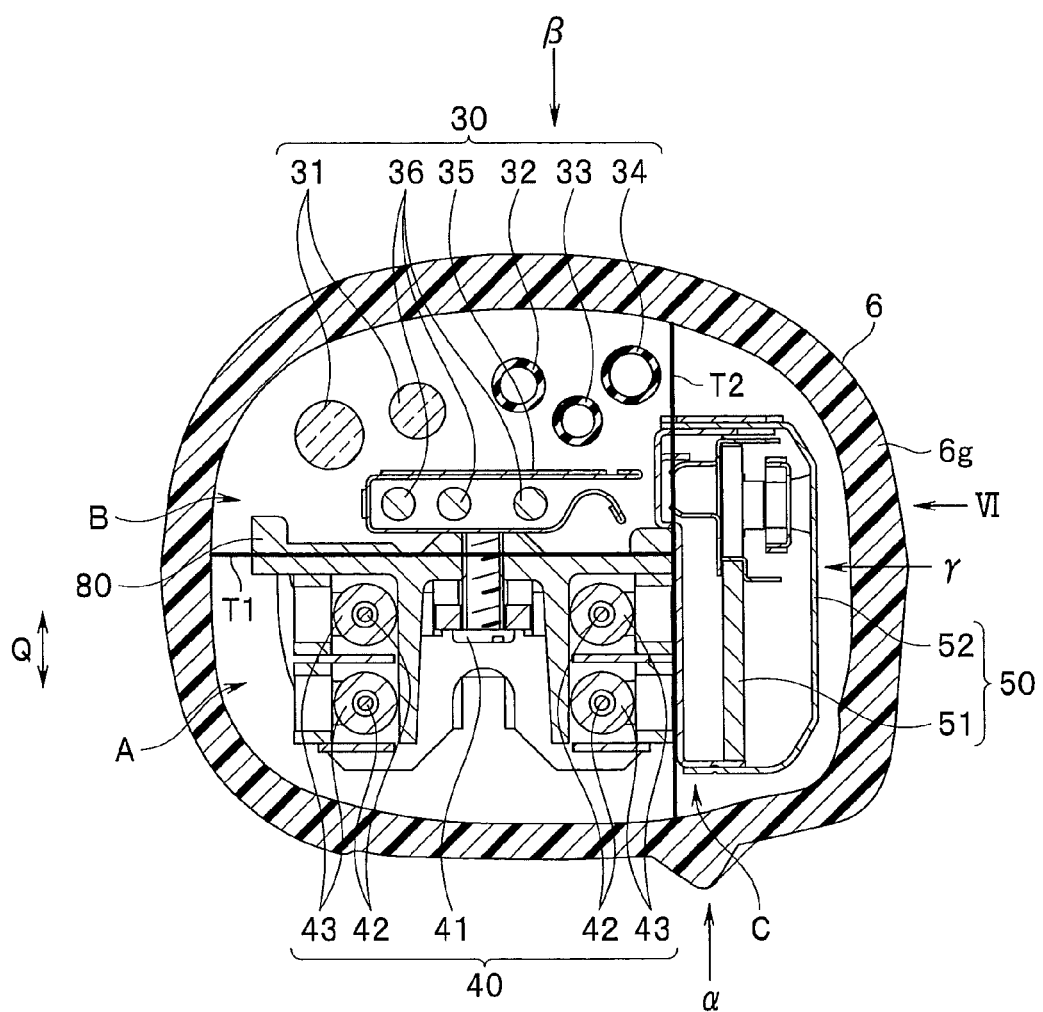
FIG. 5 is a sectional view of the operation portion along line V-V in FIG. 4.

Next, a configuration inside the grasping portion 6h of the operation portion 6 will be described using FIGS. 5-7. FIG. 5 is a sectional view of the operation portion along line V-V in FIG. 4, FIG. 6 is a view of the operation portion in FIG. 5 when viewed from direction VI in FIG. 5, and FIG. 7 is a perspective view showing a state in which the exterior member of the grasping portion of the operation portion in FIG. 1 is removed.

Figure 6:
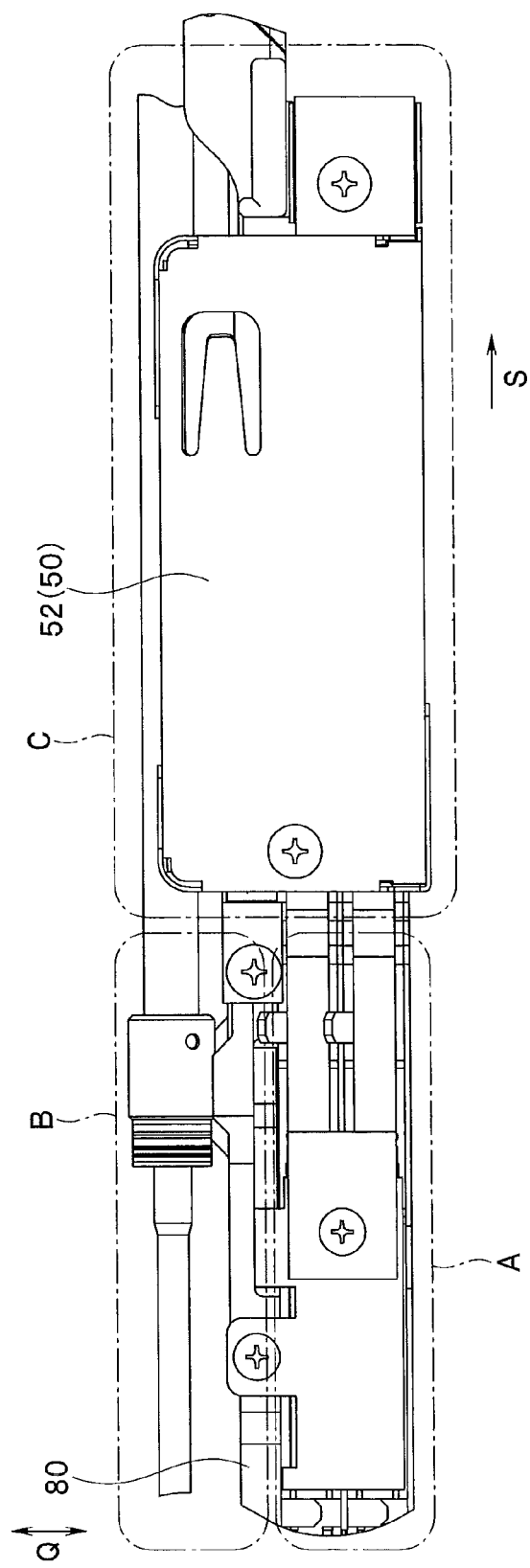
FIG. 6 is a view of the operation portion in FIG. 5 when viewed from direction VI in FIG. 5.
Figure 7:
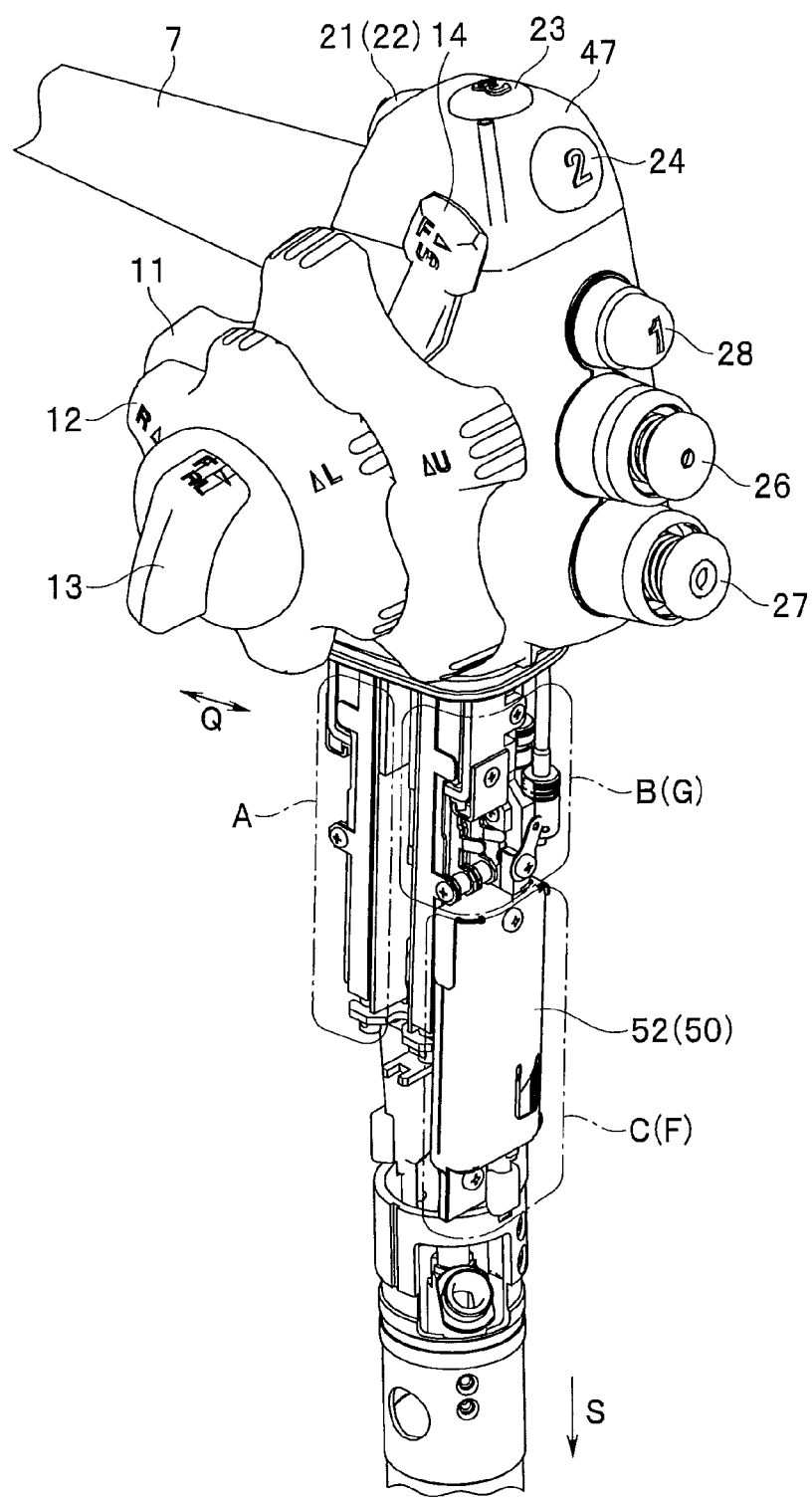
FIG. 7 is a perspective view showing a state in which an exterior member of a grasping portion of the operation portion in FIG. 1 is removed.

As shown in FIGS. 5-7, inside the grasping portion 6h of the operation portion 6, a bending drive mechanism 40 for bending the bending portion 4, flexible members 30 which are solid or hollow, elongated along the insertion direction S and inserted through at least the insertion portion 2 and the operation portion 6, and electric parts 50 are provided by being fixed to a fixing board 80 which is provided in the grasping portion 6h.

Specifically, the bending drive mechanism 40 is configured to include, as principal parts, wires 42, e.g. four in number, which are inserted through the insertion portion 2 and have distal ends fixed to the bending portion 4, coil sheaths 43 respectively covering outer circumferences of the wires 42, pulleys, not shown, on which the wires 42 are wound, screws 41 for fixing the bending drive mechanism 40 to the fixing board 80.

Further, as shown in FIGS. 5-7, the bending drive mechanism 40 is housed by being gathered to one place, i.e. only to a first housing region A in the grasping portion 6h, which is located at a position adjacent to a part where the bending operation knobs 11 and 12 are provided and on a side of the surface on which the switch buttons 21 and 22 are provided.

The flexible members 30 are configured to mainly include a light guide 31, an air feeding tube 32, a water feeding tube 33, a sub-water feeding tube 34, signal cables 36 extended from the image pickup unit and a metal shield 35 covering outer circumferences of the signal cables 36, for example, which are already known, and the metal shield 35 is fixed on a surface of the fixing board 80 which is opposite to the surface on which the bending drive mechanism 40 is fixed.

Further, as shown in FIGS. 5-7, the flexible members 30 are housed by being gathered to one place, i.e. only to a second housing region B in the grasping portion 6h, which is located at a position adjacent to the part where the bending operation knobs 11 and 12 are provided and on a side of the surface on which the switch buttons 24 and 26-28 are provided.

That is, the second housing region B is located along the first housing region A with the fixing board 80 sandwiched between the first housing region A and the second housing region B in an orthogonal direction Q orthogonal to the insertion direction S. Further, a part of the second housing region B is located in the covering region G.

The electric parts 50 is configured to mainly include an electric substrate 51 which is electrically connected to the signal cables 36 at a position in the grasping portion 6h and thereby amplifies image pickup signals being transmitted through the signal cables 36, and a shield case 52 which covers the electric substrate 51, and the shield case 52 is fixed to the fixing board 80 on an end surface orthogonal to the surfaces to which the bending drive mechanism 40 and the flexible members 30 are fixed.

Further, the electric parts 50 are housed by being gathered to one place, i.e. only to a third housing region C which is adjacent to both of the first housing region A and the second housing region B.

Specifically, the electric parts 50 are housed in the third housing region C located to be adjacent to both of the first housing region A and the second housing region B so that a first boundary line T1 between the first housing region A and the second housing region B is orthogonal to a second boundary line T2 between the first and second housing regions A and B and the third housing region C, i.e. to have a T-shape. Besides, the third housing region is located to be distal with respect to the covering region G and thereby located in the non-covering region F.

Further, in the present embodiment, the electric parts 50 are shown as being constituted by the electric substrate 51 and the shield case 52 as an example, but the electric parts 50 may be configured to include a plurality of electric components. For example, in addition to the electric substrate for amplifying the image pickup signals, it may be configured in the same manner such that a substrate for driving a light source is covered by the shield case and housed, and in this case also, a plurality of electric parts are housed by being gathered to one place of the third housing region C only.

It is noted, as shown in FIG. 5, that a housing direction α of the bending drive mechanism 40 with respect to the first housing area A, a housing direction β of the flexible members 30 with respect to the second housing region B and a housing direction γ of the electric parts 50 with respect to the third housing region C when the exterior member 6g of the grasping portion 6h is removed as shown in FIG. 7 are different from each other.

That is, fixing directions of the bending drive mechanism 40, the flexible members 30 and the electric parts 50 with respect to the fixing board 80 differ from each other.

As described, in the present embodiment, it is shown that, in the grasping portion 6h, the bending drive mechanism 40 is housed by being gathered to one place of the first housing region A only, the flexible members 30 are housed by being gathered to one place of the second housing region B only which is located to be lined up with the first housing region A along the orthogonal direction Q, and the electric parts 50 are housed by being gathered to one place of the third housing region C only which is located to be adjacent to both of the first housing region A and the second housing region B so that the first boundary line T1 is orthogonal to the second boundary line T2.

With this configuration, even though the electric parts 50 are housed in the grasping portion 6h so that a packing ratio of the parts housed in the grasping portion 6h is increased, the bending drive mechanism 40, the flexible members 30 and the electric parts 50 are respectively housed in different regions in the grasping portion 6h and not mixedly housed. Therefore, there does not arise a case where the parts interfere with each other after being housed and the flexible parts 30 are broken or the operation of the bending drive mechanism 40 is hindered by the flexible parts 30 and the electric parts 50, as mentioned above.

Further, since the housing regions differ from each other according to types of component parts, workability in housing the bending drive mechanism 40, the flexible members 30 and the electric parts 50 in the grasping portion 6h is improved.

Further, in the present embodiment, it is shown that the third housing region C in which the electric parts 50 are housed is located in the non-covering region F.

With this configuration, as shown in FIG. 2, when grasping the grasping portion 6h by the left hand L, the palm, the thumb LO, the middle finger LH, the ring finger LM and the little finger LK of the left hand L are in contact with the covering region G and do not come in contact with the non-covering region F. Therefore, even when the electric substrate 51, which is housed to be gathered to one place of the third housing region only, generates heat with driving, only the non-covering region F is heated and the covering region G is not heated. That is, since the part grasped by the fingers of the operator is not heated, it is not made difficult for the operator to grasp the grasping portion 6h for a long time.

Further, in the present embodiment, it is shown that the housing direction α of the bending drive mechanism 40 with respect to the first housing region A, the housing direction β of the flexible members 30 with respect to the second housing region B and the housing direction γ of the electric parts 50 with respect to the third housing region C are different from each other. That is, it is shown that the fixing directions of the bending drive mechanism 40, the flexible members 30 and the electric parts 50 with respect to the fixing board 80 are different from each other.

With the foregoing, when fixing the bending drive mechanism 40, the flexible members 30 and the electric parts 50, in a work of housing the bending drive mechanism 40 in the first housing region A, for example, if the housing direction is the same as those of the flexible members 30 and the electric parts 50, the bending drive mechanism cannot be housed unless the work is performed according to a housing sequence so that workability has been lowered, e.g. the bending drive mechanism has to be housed after moving the flexible members 30 and the electric parts 50 which are already housed. However, according to the present embodiment, since the housing directions of the respective parts with respect to the hosing regions are different from each other, the flexible members 30 and the electric parts 50 which are housed in the other housing regions B and C, respectively, do not hinder the housing work of the bending drive mechanism 40. This situation is the same as that in housing the flexible members 30 and the electric parts 50. Thus, irrespective of the housing sequence, the fixing work of the bending drive mechanism 40, the flexible members 30 and the electric parts 50 with respect to the fixing board 80 can be performed.

As described above, it is possible to provide the endoscope 1 in which the interference between the respective parts in the operation portion 6 can be prevented even though the electric parts 50 are housed in the operation portion 6 so that a packing ratio of the parts housed in the operation portion 6 is increased, and workability in assembling the respective parts in the operation portion 6 is made easy, and further the operation portion 6 can be prevented from being made difficult to grasp for a long time.

Figure 8:
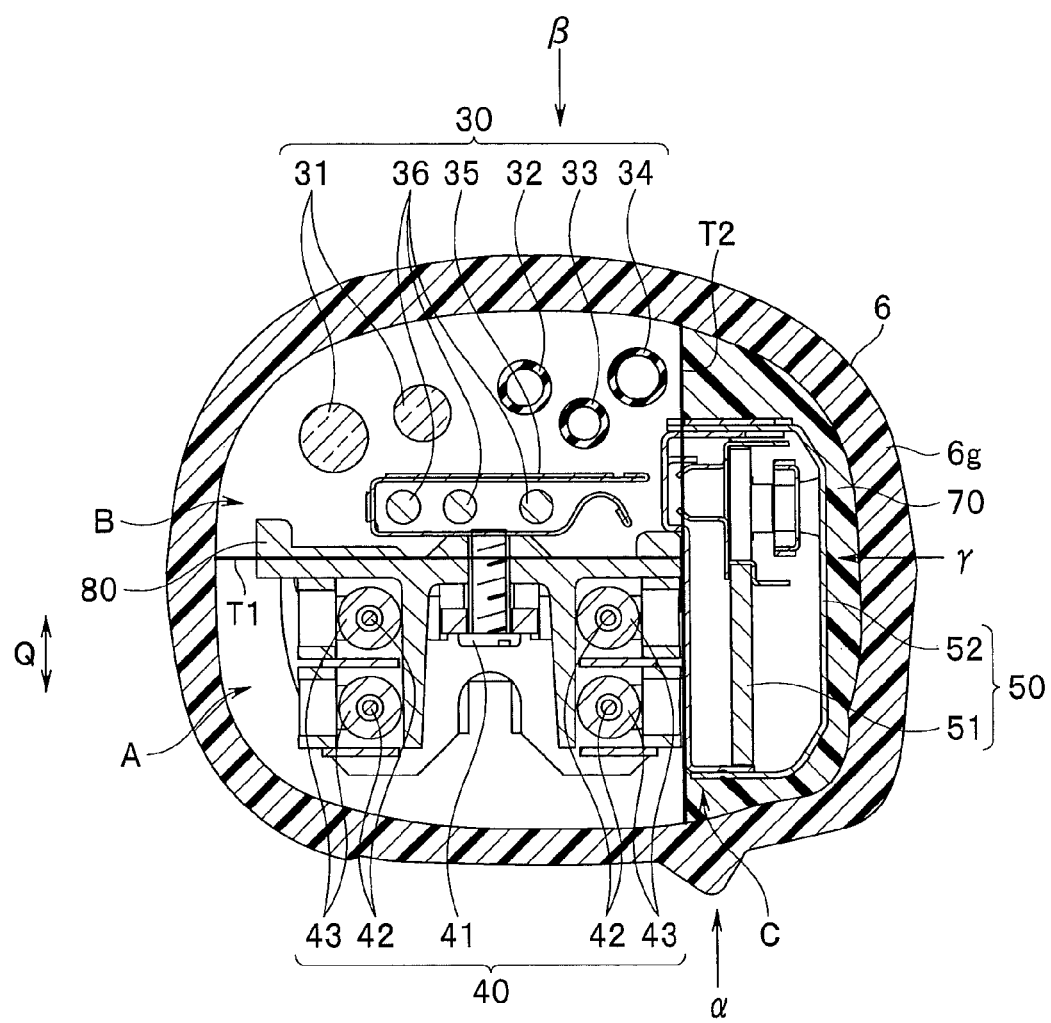
FIG. 8 is a sectional view showing a modified example in which a heat conduction member is interposed between electric parts and the exterior member of the grasping portion.

Besides, a modified example is shown below using FIG. 8. FIG. 8 is a sectional view showing the modified example in which a heat conduction member is interposed between the electric parts and the exterior member of the grasping portion.

As described in FIG. 8, a heat conduction member, specifically an elastic member 70 having heat conductivity may be interposed between an outer periphery of the shield case 52 of the electric parts 50 and the exterior member 6g of the grasping portion 6h in the non-covering region F.

With this configuration, the heat of the electric substrate 51 can be positively conducted through the elastic member 70 to the non-covering region F of the exterior member 6g.

Further, a heat insulation member, other than the heat conduction member, may be interposed between the outer periphery of the shield case 52 and the exterior member 6g of the grasping portion 6h in the non-covering region F.

Furthermore, in the present embodiment, since the electric parts 50 are gathered and housed in one place of the third housing region C only, it is sufficient to take a countermeasure for heat of the electric parts 50 using the heat conduction member or the heat insulation member, as described and shown in FIG. 8, at one location only. It is noted that the forgoing is also applicable to a case where the electric parts include a plurality of electric components.

This is because, if the plurality of electric parts 50 are interspersed inside the grasping portion 6h, countermeasures for the heat have to be taken for the respective electric parts. However, if it is configured such that the plurality of electric parts are gathered and housed in one place of the third housing region only according to the present embodiment, and countermeasure for the heat may be taken at one location only, so that the workability in assembling is improved. Besides, this is also applicable to a case where outer peripheries of the electric parts are covered by heart radiation sheets or the like.

The other effects are the same as those of the above-described embodiment.

Second Embodiment

Figure 9:
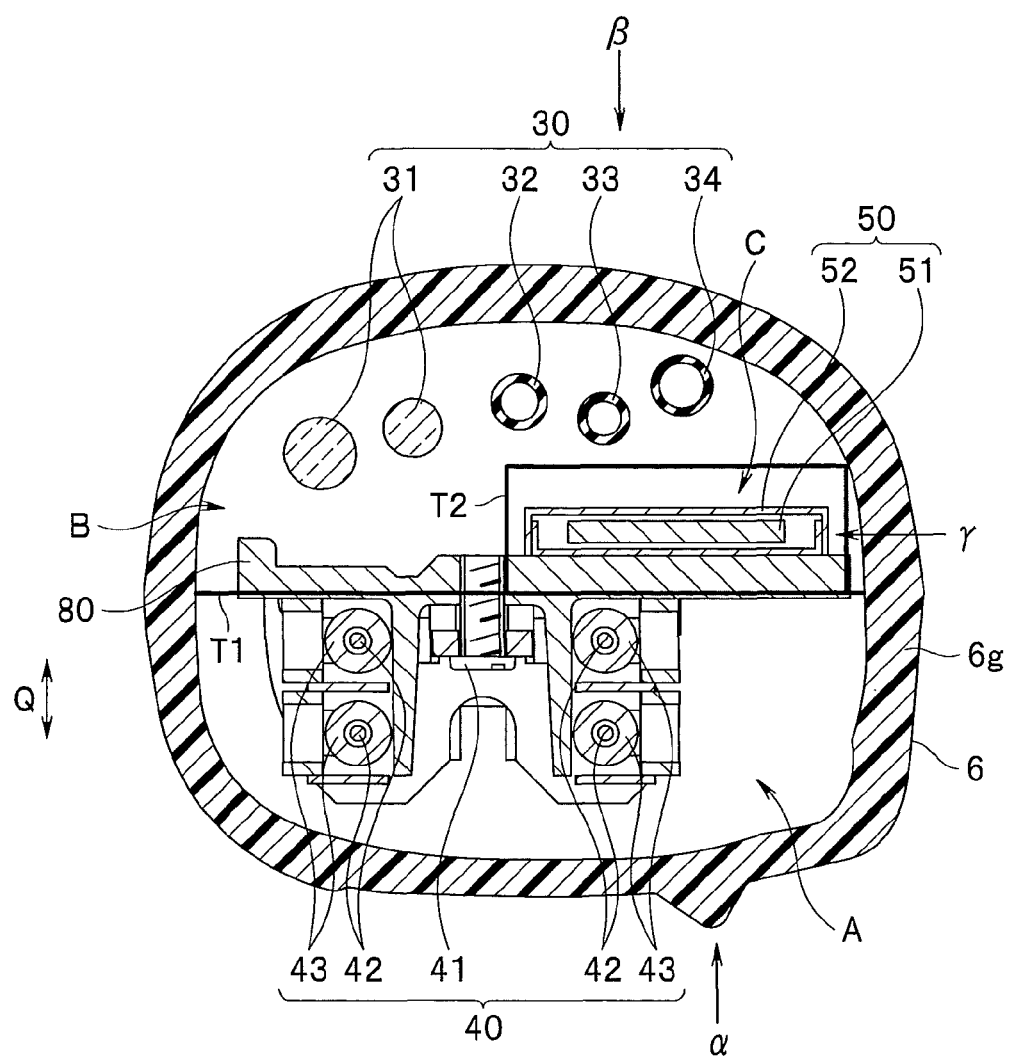
FIG. 9 is a sectional view showing a configuration in which electric parts are fixed to a fixing board so that an electric substrate is parallel to the fixing board in an endoscope according to a second embodiment of the present invention.

FIG. 9 is a sectional view showing a configuration in which the electric parts are fixed to the fixing board so that the electric substrate is parallel to the fixing board in an endoscope according to a second embodiment of the present invention.

The configuration of the endoscope according to the second embodiment differs from that of the endoscope according to the first embodiment as described and shown in FIGS. 1-7 in that the electric parts are fixed to the fixing board so that the electric substrate is parallel to the fixing board. Therefore, the same reference sign is assigned to the configuration similar to that in the first embodiment and description thereof is omitted.

In the above-described first embodiment, it is shown that the electric parts 50 are housed in the third housing region C located to be adjacent to both of the first housing region A and the second housing region B so that the first boundary line T1 between the first housing region A and the second housing region B is orthogonal to the second boundary line T2 between the first and second housing regions A and B and the third housing region C, i.e. to have a T-shape, and the shield case 52 is fixed to the end surface of the fixing board 80 orthogonal to the surfaces to which the bending drive mechanism 40 and the flexible members 30 are fixed.

The configuration is not limited to the above and, as shown in FIG. 9, the third housing region C may be located in the second housing region B, and the electric parts 50 may be housed in the third housing region C with the shield case 52 being fixed to the same surface of the fixing board 80 on which the flexible member 30 is fixed so that the electric substrate 51 is parallel to the fixing board 80.

It is noted that, in this configuration also, the third housing region C in the second housing region B has to be located within the non-covering region F.

Further, the third housing region C may be located in the second housing region B, as described above, but it is not preferable that the third housing region C is located in the first housing area A. This is because the operation of the bending drive mechanism 40 is hindered if a component removed from the electric parts 50 comes in contact with the bending drive mechanism 40.

Furthermore, in the present embodiment, the shield case 52 may be fixed to the fixing board 80 by sliding the electric parts 50 in the housing direction γ in parallel to the fixing board 80.

With the above configuration, the electric parts 50 housing in the third housing region C are arranged inside to be farther from the exterior member 6g in the grasping portion 6h than the electric parts in the above-described first embodiment, and therefore the grasping portion is made more difficult to be heated.

The other effects are the same as those of the above-described first embodiment.

Third Embodiment

Figure 10:
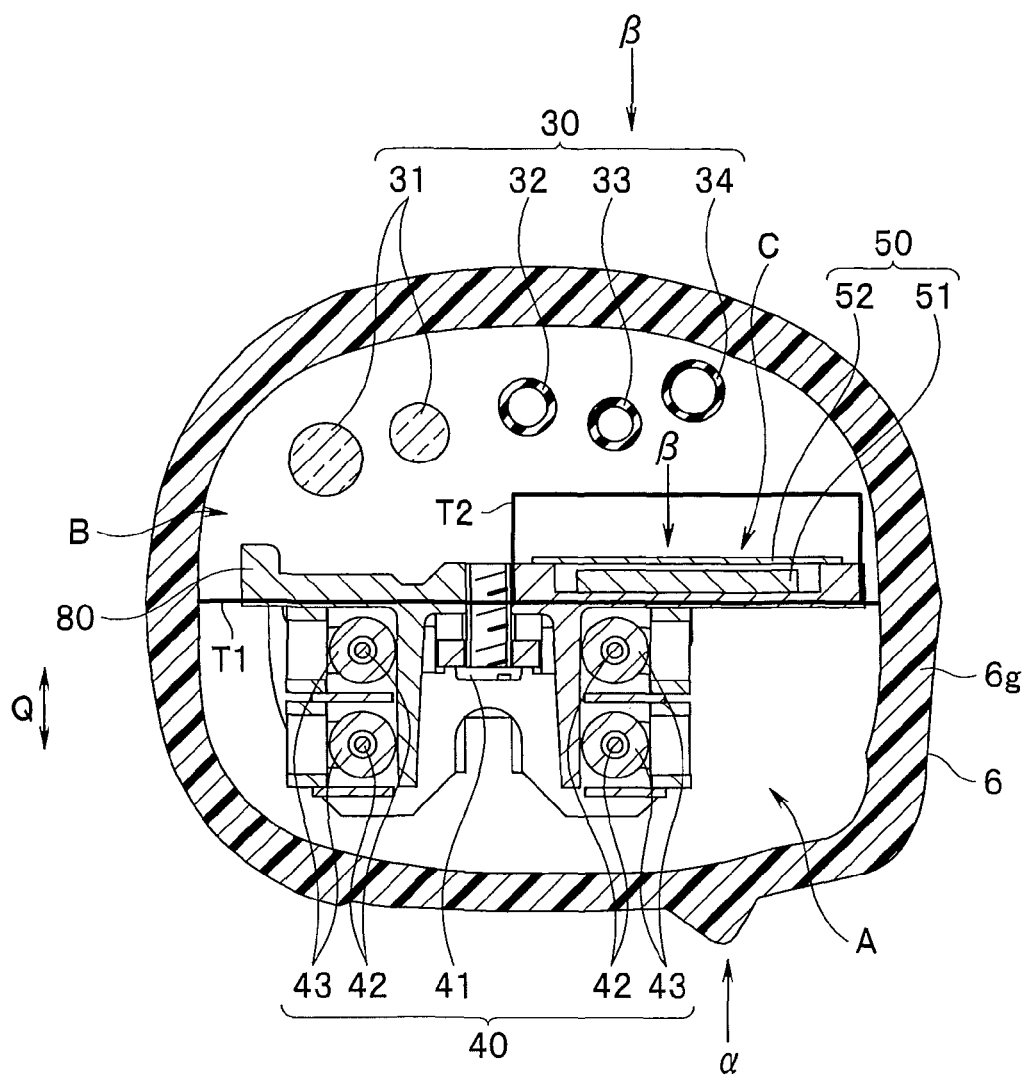
FIG. 10 is a sectional view showing a configuration in which a fixing board is formed integrally with a shield case of an electric component in an endoscope according to a third embodiment of the present invention.

FIG. 10 is a sectional view showing a configuration in which the fixing board is formed integrally with the shield case of the electric parts in an endoscope according to the present third embodiment.

The configuration of the endoscope according to the third embodiment differs from the endoscope according to the above-described second embodiment shown in FIG. 9 in that the fixing board shown in FIG. 9 is formed integrally with the shield case of the electric parts. Therefore, the same reference sign is assigned to the configuration similar to that in the second embodiment and description thereof is omitted.

In the above-described second embodiment, it is shown the shield case 52 is fixed to the same surface of the fixing board 80 on which the flexible members 30 are fixed.

The configuration is not limited to the above and the third housing region C may be located in the second housing region B in the same manner as the second embodiment as shown in FIG. 9, and further the electric parts 50 may be housed in the third housing region C so that the electric substrate 51 is parallel to the fixing board 80 with the shield case 52 being formed integrally with the fixing board 80.

Besides, in this configuration also, it is necessary that the third housing region C in the second housing region B is located within the non-covering region F.

Further, in the present embodiment, the housing direction of the electric parts 50 with respect to the third housing region C may be the same as the housing direction β of the flexible members 30 with respect to the second housing region B. That is, it is not necessary that all the housing directions of the respective parts with respect to the three housing areas are different from each other and in the case where the two housing regions are overlapped as in the present embodiment, the housing directions with respect to the overlapped housing regions may be the same.

With the above configuration, the same effects can be obtained as the above-described second embodiment. It is noted that the other effects are the same as the above-described second embodiment.

The present invention is not limited to the foregoing embodiments and various changes, modifications and the like are possible within a range in which the gist of the present invention is not changed.

What is claimed is:

1. An endoscope comprising:
an insertion portion to be inserted into a subject;
an operation portion which is provided in series at a proximal end side in an insertion direction of the insertion portion so as to extend along the insertion direction and which is configured to be grasped and operated by an operator;
a bending portion provided at a distal end side of the insertion portion;
a first housing region which is set in the operation portion;
a second housing region which is adjacent to the first housing region along a direction orthogonal to the insertion direction;
a third housing region which is adjacent to the first housing region and the second housing region along the direction orthogonal to the insertion direction;
a bending drive mechanism including a bending operation wire for bending the bending portion, the bending drive mechanism being housed in the first housing region and inserted into the insertion portion and the operation portion, to be extended along the insertion direction;
a flexible member including a signal cable and a fluid conduit, the flexible member being housed in the second housing region and inserted into the insertion portion and the operation portion, to be extended along the insertion direction; and
an electric part housed in the third housing region and including a substrate for amplifying an image pickup signal being transmitted through the signal cable, the substrate having a plane which extends along the insertion direction;
a fixing board provided in the operation portion, and having a plane defining a boundary between the first housing region and the second housing region; and
a shield case provided in the operation portion and fixed to the fixing board, the shield case having a wall surface a part of which is orthogonal to the plane of the fixing board to thereby define a boundary between the first and second housing regions and the third housing region, wherein the shield case houses the electric part including the substrate and forms an air space between an inner surface and a surface of the substrate, and
wherein the third housing region is arranged in a non-covering region which is not in contact with fingers of an operator when an exterior member of the operation portion is grasped by the operator, the non-covering region being different from a covering region of the exterior member which is in contact with and covered by the fingers of the operator when the exterior member of the operation portion is grasped by the operator.

2. The endoscope according to claim 1, wherein the electric part is mounted to a surface of the substrate that faces the exterior member of the operation portion.

3. An endoscope comprising:
an insertion portion configured to be inserted into a subject;
an operation portion housing connected in series to the insertion portion;
a bending drive mechanism configured to transmit a bending force to the insertion portion to bend the insertion portion;
a signal line configured to transmit a signal from the insertion portion to the operation portion housing;
an electric circuit configured to process the signal transmitted by the signal line;
an input mechanism arranged at a proximal end of the operation portion housing, wherein the input mechanism is configured to receive a user input from a finger of a hand as another portion of the hand grasps an intermediate portion of the operation portion housing between the proximal end of the operation portion housing and a distal end of the operation portion housing connected to the insertion portion,
wherein an end of the bending drive mechanism and an end of the signal line terminate at only a first interior space defined within the intermediate portion of the operation portion housing, and
wherein the electric circuit is situated at only a second interior space defined within the intermediate portion of the operation portion housing, wherein the second interior space is arranged to be further from the input mechanism than the first interior space to reduce transfer of heat generated by the electric circuit to the another portion of the hand grasping the intermediate portion of the operation portion housing.

4. The endoscope according to claim 3, further comprising a bending knob provided adjacent to the input mechanism,
wherein the bending knob is operatively connected to the end of the bending drive mechanism, and is configured to be rotated by the finger of the hand to generate the bending force that is transmitted by the bending drive mechanism to bend the insertion portion, as the another portion of the hand grasps the intermediate portion of the operation portion housing.

5. The endoscope according to claim 3, further comprising an electric substrate on which the electric circuit is disposed.

6. The endoscope according to claim 5,
wherein the insertion portion and the operation portion housing are connected in series along an insertion direction,
wherein the endoscope further comprises a fixing board arranged in the operation portion housing and extending in the insertion direction, wherein the fixing board comprises a first surface, a second surface opposing the first surface, and a third surface orthogonal to the first surface and the second surface, and
wherein when viewing a cross-section of the operation portion housing at the first interior space along the insertion direction towards the insertion portion,
the first surface and the second surface oppose each other in a direction orthogonal to the insertion direction,
the bending drive mechanism is attached to the first surface of the fixing board,
the signal line is attached to the second surface of the fixing board, and
the electric circuit is attached to the third surface of the fixing board.

7. The endoscope according to claim 3, further comprising an electric circuit shield case,
wherein the electric circuit is arranged within the electric circuit shield case.

8. The endoscope according to claim 7,
wherein an outer surface of the electric circuit shield case is separated from an inner surface of the operation portion housing by a predetermined distance.

9. The endoscope according to claim 6, further comprising an electric circuit shield case,
wherein the electric circuit is arranged within the electric circuit shield case, and
wherein the electric circuit shield case is attached to the third surface of the fixing board.

10. The endoscope according to claim 3, further comprising a metal shield,
wherein at least a portion of the signal line is arranged within the metal shield.

11. The endoscope according to claim 10, further comprising one or more of a light guide, an air feeding tube, a water feeding tube, and a sub-water feeding tube, arranged between an outer surface of the metal shield and an inner surface of the operation portion housing.

12. The endoscope according to claim 11,
wherein the one or more of the light guide, the air feeding tube, the water feeding tube, and the sub-water feeding tube are flexible.

13. The endoscope according to claim 6, further comprising a metal shield,
wherein at least a portion of the signal line is arranged within the metal shield, and
wherein the metal shield is attached to the second surface of the fixing board.

* * * * *